United States Patent [19]

Barbuscio et al.

[11] 4,313,393
[45] Feb. 2, 1982

[54] INDICATOR DEVICE FOR DETECTING THE AMOUNT OF SEBUM IN HAIR AND SCALP AND METHOD THEREFOR

[75] Inventors: Frank D. Barbuscio, Wayne; LeRoy Hunter, Randolph; Joseph C. Hourihan, Little Falls; Mary C. Inglis, Nutley; Helen E. Oberstar, Montville; Hosny Saad, Ramsey, all of N.J.

[73] Assignee: American Cyanamid Company, Stamford, Conn.

[21] Appl. No.: 943,909

[22] Filed: Sep. 19, 1978

Related U.S. Application Data

[63] Continuation of Ser. No. 746,452, Dec. 1, 1976, abandoned.

[51] Int. Cl.³ ............................................. G01N 21/01
[52] U.S. Cl. .................................... 116/200; 116/206; 424/7
[58] Field of Search ....................... 116/200, 201, 206; 424/9, 7; 73/356; 23/230 B, 230 L

[56] References Cited

U.S. PATENT DOCUMENTS

| B 426,424 | 2/1976 | Rey et al. | 424/9 |
| 2,379,459 | 7/1945 | Schreiber et al. | 73/356 |
| 2,918,893 | 12/1959 | Norton | 116/206 |
| 3,006,735 | 10/1961 | Jordan | 23/230 R |
| 3,298,789 | 1/1967 | Mast | 23/230 B |
| 3,317,283 | 5/1967 | King | 116/114 R |

FOREIGN PATENT DOCUMENTS

1171869 11/1969 United Kingdom ............... 116/200

*Primary Examiner*—Daniel M. Yasich
*Attorney, Agent, or Firm*—Charles J. Fickey

[57] ABSTRACT

An indicating device for determining the dry, normal or oily characteristics of human hair and scalp. More particularly, an indicating device comprising an oil absorbent indicating material, treated with an oil-soluble dye, surrounded by an oil permeable membrane. The invention additionally relates to a method for determining the dry, normal or oily characteristics of the hair and scalp.

1 Claim, 2 Drawing Figures

INDICATOR DEVICE FOR DETECTING THE AMOUNT OF SEBUM IN HAIR AND SCALP AND METHOD THEREFOR

This is a continuation of application Ser. No. 746,452, filed Dec. 1, 1976, now abandoned.

This invention relates to an indicating device for determining the dry, normal or oily characteristics of human hair and scalp. More particularly, it relates to an indicating device comprising an oil absorbent indicating material, treated with an oil-soluble dye, surrounded by an oil permeable membrane. The invention additionally relates to a method for determining the dry, normal or oily characteristics of the hair and scalp.

Human hair (and scalp) varies considerably in the degree to which it is oily. The sebaceous glands of the skin (scalp) secrete sebum (fatty acids and esters, mainly) to a greater or lesser extent in all humans. The hair is thereby characterized as either dry, normal or oily, depending on the extent of this secretion of the scalp. The composition of hair cleansing formulations (shampoos) will, or should, vary depending on whether the user has dry, normal or oily hair. The problem is that many people do not know, or are not sure, which type of shampoo is best suited to their needs. It would, therefore, be highly desirable to make available to the public a simple, inexpensive, reliable indicating device which, when rubbed on the hair and scalp, would indicate the extent of sebum or whether their hair had dry, normal or oily characteristics (hereafter referred to as D/N/O characteristics of the hair). The indicator device should also enable the user to estimate the degree of oiliness on some arbitrary scale.

It is the essential purpose of the invention to provide such an indicating device and a method for estimating the D/N/O characteristics of the hair and scalp.

For a fuller understanding of the nature and objects of the invention, reference should be made to the following detailed description taken in connection with the drawings wherein.

Figure 1:
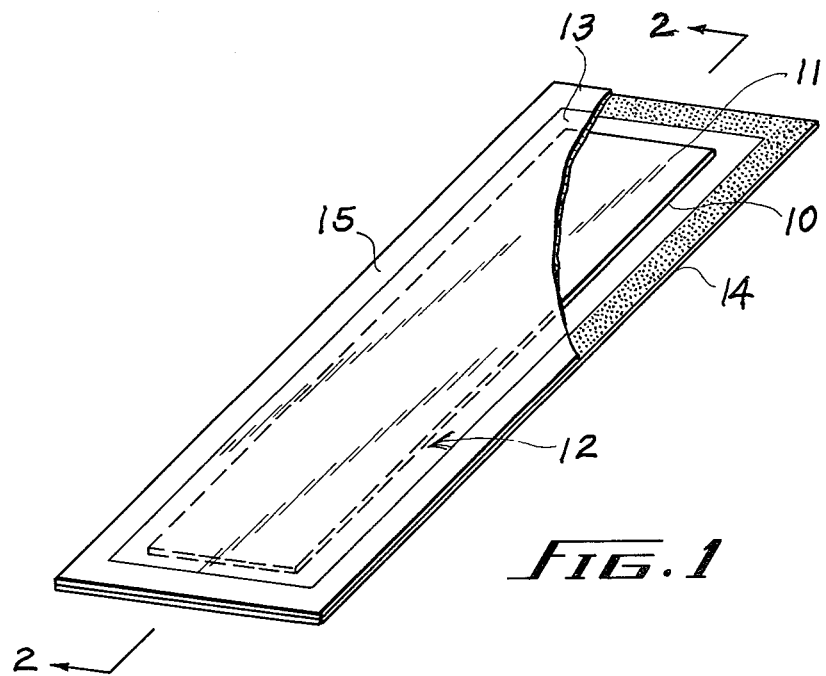
FIG. 1 is a perspective view of the indicator with parts broken away.
Figure 2:
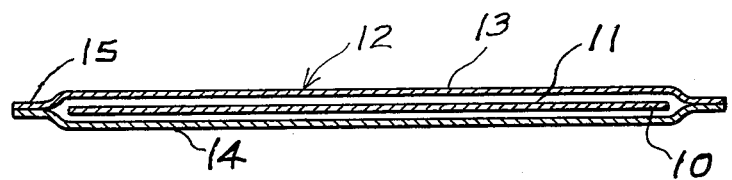
FIG. 2 is a cross-sectional side view taken along the lines 2—2 of FIG. 1.

In accordance with the above purposes, we have invented a simple, inexpensive, reliable indicator device for determining the D/N/O characteristics of the hair and scalp which comprises a suitable oil absorbent material 10, capable of absorbing oil (sebum) from the hair and scalp, said absorbent material being treated with an oil-soluble dye 11 which will dissolve in said sebum, and an oil permeable membrane 12 surrounding said dyed absorbent material; the oil permeable membrane being such that the oil is able to permeate thru to the inner oil absorbent material, and the oil absorbent material being such that the oil absorbed thereon will not re-permeate thru the membrane.

The oil permeable membrane 12 is adjacent the dyed surface 11, and may consist of an entire envelope. However, the oil permeable membrane 12 consists of a single membrane 13 joined and sealed at edges 15 to a second member 14 which does not necessarily need to be oil permeable.

Simply stated, an oil absorbent material, such as paper, non-woven fabric or a fabric, is treated with an oil soluble dye on at least one surface. The oil absorbent material so dyed is then covered with a suitable oil-permeable membrane, such as paper, non-woven fabric, fabric, polymer film, or the like, which permits the sebum to penetrate thru to the oil absorbent material. The sebum then dissolves all or part of the dye with which it comes in contact, causing a color change or spot thereon, which varies in size and color, depending on the amount of sebum absorbed and the type of dye or dyes used. The extent of oil in the hair and scalp is then estimated using an arbitrary scale depending on the size and color of the spot, and on the solubility of the dye in the oil.

Any suitable material may be used to form the oil absorbing layer, so long as it absorbs the sebum to the extent that it will not allow the sebum to permeate back through the covering oil permeable membrane. The purpose of the oil absorbent material is to (1) hold the oil soluble dye, (2) absorb the sebum, (3) retain the oil (sebum) solubilized dye, and (4) to allow wicking of the oil solubilized dye within the absorbent material. While any number of materials may be found suitable for use as the absorbent material, consistent with the stated functions, we have obtained excellent results with Whatman No. 4 Chromatographic Paper and Kimberly-Clark BP156 nonwoven fabric (paper). These absorbents are preferred for use in the indicating device of this invention, but the invention is not limited thereto, since any absorbent material meeting the stated requirements are believed to be suitable for use.

The paper, etc. which is used as the absorbent material, is treated with an oil soluble dye, e.g., by saturating the material with the dye, or treated so that the dye covers only one side of the material. The material may be treated as described using one dye or with two or more dyes. The dyes may be oil-soluble, oil-insoluble or have varying degrees of oil solubility provided there is at least one dye with oil-solubility. The absorbent paper dyed with the dye may be applied to a suitable backing material so that only one dyed side thereof is exposed to the oil-permeable membrane, or the paper so treated may be completely enclosed by or surrounded by an envelope of the oil permeable membrane. Many such combinations may be envisioned and are contemplated for use in the invention, it not being critical how the co-acting members of the indicating device are assembled so long as the oil absorbent material is not directly in contact with the hair and scalp.

Any oil-soluble dye which will provide sufficient depth of color to observe a visual change may be used. As indicated, the absorbent material, which may be white or colored, may be dyed with one or a mixture of dyes, at least one of which must be an oil-soluble dye soluble in the sebum. Dissolution of the oil-soluble dye in the sebum in any case must result in a visual change.

A particularly useful dye is Calco Oil Red Z1700 (C.I. Solvent Red 26, C.I. No. 26120). When used with white absorbent paper, this dye changes color from red through shades of pink to white, depending on the amount of oil absorbed. The color of the dye used, however, is not critical and a variety of oil-soluble dyes, partially oil-soluble dyes, and oil-insoluble dyes may be used, provided at least one oil-soluble is present.

The oil-permeable membrane covering material, as stated above, may be paper, non-woven fabrics, fabrics, polymer films, etc. so long as the sebum is able to penetrate thru to the dyed oil-absorbent material. The oil-permeable membrane (or covering material) has the functions (1) to prevent contact of the skin/hair and the dyed oil-absorbent material; (2) to allow the sebum to reach the oil-absorbent material; and (3) to prevent the oil solubilized dye from migrating from the oil absorbent material to the skin.

The means used to assess the degree of oil (sebum) in the hair/scalp is one which compares the type of color change, the degree of color change and/or the size of the spot on the oil absorbent paper, with a standardized comparison chart.

Although the indicating device of the present invention is primarily directed to use in determining the degree of oiliness of hair and scalp, it is also applicable to a determination of the degree of oiliness of the skin, particularly the facial skin around the eyes, nose and forehead.

We claim:

1. An indicator device for contact with human hair or scalp for determining the oiliness thereof, comprising (a) an oil-absorbent sheet material capable of absorbing sebum from the hair and scalp, said oil-absorbing sheet material being dyed on a surface with (b) an oil-soluble dye, soluble in sebum, capable of giving a visual physical color change in the area when placed in contact with sebum to form a spot of differing color when the dye dissolves the sebum of a size proportional to the amount of sebum absorbed by the oil-absorbing material, and (c) a non-adhering oil-permeable transparent sheet material permeable to said sebum adjacent to and superimposed over said dyed surface, said oil-permeable sheet forming part of an envelope enclosing said dyed oil-absorbent sheet, and allowing passage of sebum when brought into contact with sebum, whereby said sebum is absorbed by said absorbent sheet material to effect said visual physical color change which is visible through said transparent envelope surface.

* * * * *